United States Patent
Scott et al.

(10) Patent No.: US 6,887,307 B1
(45) Date of Patent: May 3, 2005

(54) PULLULAN FILM COMPOSITIONS

(75) Inventors: Robert Scott, Sint Niklaas (BE);
Dominique Cade, Colmar (FR);
Xiongwei He, Andolsheim (FR)

(73) Assignee: Warner-Lambert Company, LLC, Morris Plains, NJ (US)

( * ) Notice: Subject to any disclaimer, the term of this patent is extended or adjusted under 35 U.S.C. 154(b) by 132 days.

(21) Appl. No.: 10/031,897

(22) PCT Filed: Jul. 18, 2000

(86) PCT No.: PCT/EP00/06843

§ 371 (c)(1),
(2), (4) Date: Jan. 22, 2002

(87) PCT Pub. No.: WO01/07507

PCT Pub. Date: Feb. 1, 2001

(30) Foreign Application Priority Data

Jul. 22, 1999 (EP) .............................. 99401849
May 16, 2000 (EP) .............................. 00401333

(51) Int. Cl.[7] .................. C08L 5/00; C09D 105/00; A61K 9/36; A61K 9/48
(52) U.S. Cl. ................ 106/205.01; 106/205.2; 106/205.3; 106/205.6; 106/206.71; 106/205.9; 524/55; 424/451; 424/463; 424/479
(58) Field of Search ............ 106/205.01, 205.2, 106/205.3, 205.6, 205.71, 205.9; 524/55; 424/451, 463, 479

(56) References Cited

U.S. PATENT DOCUMENTS

| | | | |
|---|---|---|---|
| 3,784,390 A | | 1/1974 | Hijiya et al. ............... 106/139 |
| 3,871,892 A | * | 3/1975 | Hijiya et al. ............. 106/135.1 |
| 4,623,394 A | | 11/1986 | Nakamura et al. ......... 106/122 |
| 6,517,865 B2 | * | 2/2003 | Cade et al. ................ 424/451 |
| 2001/0024678 A1 | * | 9/2001 | Scott et al. ................. 426/656 |
| 2001/0043999 A1 | * | 11/2001 | Scott et al. ................ 428/36.6 |
| 2002/0187190 A1 | * | 12/2002 | Cade et al. ................ 424/480 |
| 2003/0035841 A1 | * | 2/2003 | Dzija et al. ................ 424/488 |
| 2003/0054039 A1 | * | 3/2003 | Zyck et al. ................ 424/488 |

FOREIGN PATENT DOCUMENTS

| | | |
|---|---|---|
| EP | 0328317 | 8/1989 |
| JP | 53079972 | 7/1978 |
| JP | 63164858 | 7/1988 |
| JP | 63287544 | 11/1988 |
| JP | 1168619 | 7/1989 |
| JP | 2000205 | 1/1990 |
| JP | 2015026 | 1/1990 |
| JP | 3012231 | 1/1991 |
| JP | 3053873 | 3/1991 |
| JP | 3130051 | 6/1991 |
| JP | 04363332 | 12/1992 |
| JP | 4363332 | 12/1992 |
| JP | 5065222 | 3/1993 |
| JP | 05065222 | 3/1993 |
| JP | 7223952 | 8/1995 |
| JP | 11049668 | 2/1999 |
| JP | 20000202003 | 7/2000 |
| WO | 9933924 | 7/1999 |

* cited by examiner

Primary Examiner—Helene Klemanski
(74) Attorney, Agent, or Firm—Evan J. Federman; Kenneth G. Lemke

(57) ABSTRACT

The invention concerns compositions based on pullulan and a setting system for the use in pharmaceutical, veterinary, food, cosmetic or other products like films for wrapping food, aspics or jellies, preferably for predosed formulations like soft or hard capsules. The composition preferably further contains a surfactant. By using aqueous solution of the inventive compositions, the hard pullulan capsules are produced by a conventional dipping moulding process under the same process condition range than conventional gelatine capsules.

46 Claims, 1 Drawing Sheet

PULLULAN FILM COMPOSITIONS

Figure 1:
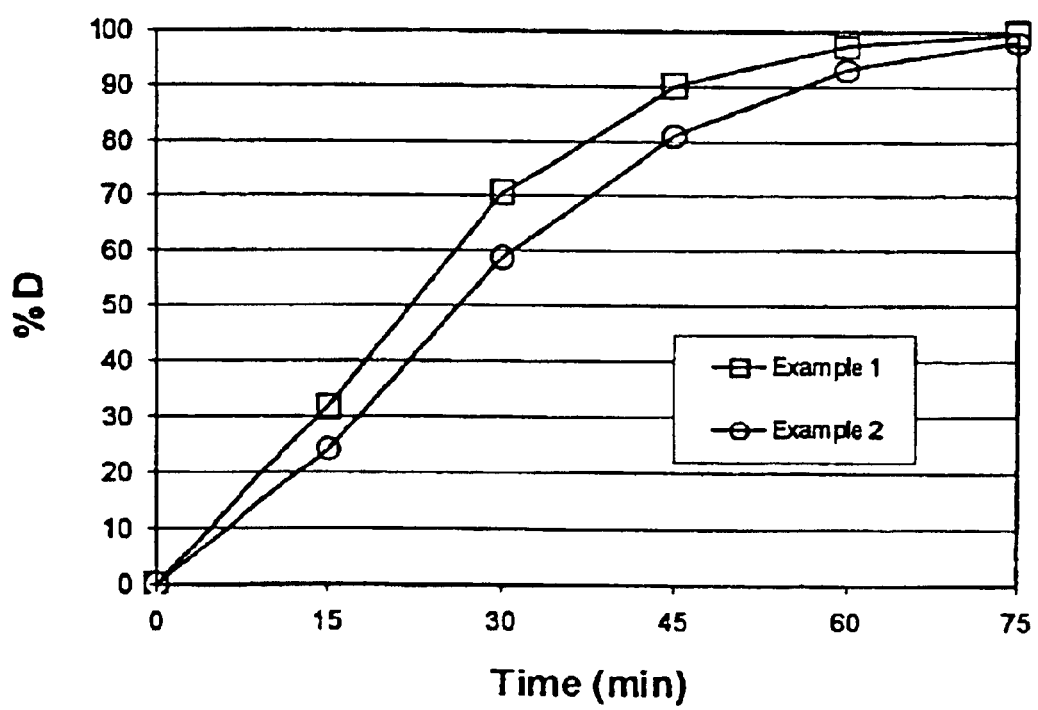

The invention concerns pullulan compositions for the use in pharmaceutical, veterinary, food, cosmetic or other products like films for wrapping food, aspics or jellies, preferably for predosed formulations like soft or hard capsules.

Conventional hard capsules are made with gelatin by dip moulding process. The dip molding process is based on the setting ability of hot gelatine solutions by cooling. For the industrial manufacture of pharmaceutical capsules gelatine is most preferred for its gelling, film forming and surface active properties. The manufacture of hard gelatin capsules by dip moulding process exploits fully its gelling and film forming abilities. A typical dip moulding process comprises the steps of dipping mould pins into a hot solution of gelatin, removing the pins from the gelatine solution, allowing the gelatine solution attached on pins to set by cooling, drying and stripping the so-formed shells from the pins. The setting of the solution on the mould pins after dipping is the critical step to obtain a uniform thickness of the capsule shell.

On a totally automatic industrial hard gelatine capsule machine, the process consists to dip mould pins into hot gelatine solution, to remove the pins from the solution, to turn the pins from downside to upside, to dry the gelatine solution (gel) attached on the pins, to strip the capsule shell and finally to cut and pre-joint the cap and body. The immediate setting of the gelatine solution on the dip pins after dipping is the key step in the process. Otherwise, the gelatin. solution would. flow down, leading to a very low top thickness, and no capsule of quality could be produced.

Attempts have been made to manufacture capsules with materials other than gelatine, notably with modified cellulose. Successful industrial examples are the capsules made of hydroxypropyl methylcellulose (HPXC).

Pullulan is a natural, viscous polysaccharide extracellularly produced by growing certain yeasts on starch syrups. It has good film forming properties and a particularly low oxygen permeability. Its existence was reported for the first time in 1938. Hayashibara Company started the commercial production in 1976.

There are numerous patents about the use of pullulan in moulded articles, edible films, and coatings.

U.S. Pat. No. 4,623,394 describes a molded article which exhibits a controlled desintegrability under hydrous conditions. The composition of the molded article consists essentially of a combination of pullulan and a heteromannan, the amount of heteromannan being, based on the dry solids, 1 to 100% of the pullulan.

JP5-65222-A describes a soft capsule, capable of stabilizing a readily oxidizable substance enclosed therein, exhibiting easy solubility, and being able to withstand a punching production method. The soft capsule is obtained by blending a capsule film substrate such as gelatin, agar, or carrageenan with pullulan.

U.S. Pat. No. 3,784,390-A, corresponding to FR 2,147, 112 and GB 1,374,199, discloses that certain mixtures of pullulan with at least one member of the group consisting of amylose, polyvinyl alcohol, and gelatine can be shaped by compression molding or extrusion at elevated temperatures or by evaporation of water from its aqueous solutions to form shaped bodies, such as films or coatings. To retain the valuable properties of pullulan to an important extent the mixture should not contain more than 120 percent amylose, 100 percent polyvinyl alcohol, and/or 150 percent gelantine based on the weight of the pullulan in the mixture.

U.S. Pat. No. 4,562,020, discloses a continuous process for producing a self-supporting glucan film, comprising casting an aqueous glucan solution on the surface of a corona-treated endless heat-resistant plastic belt, drying the glucan solution thereon while heating and releasing the resultant self-supporting glucan film. Suitable glucans are those which substantially consist of repeating maltotriose units, such as pullulan or elsinan.

JP-60084215-A2 discloses a film coating composition for a solid pharmaceutical having improved adhesive properties on the solid agent. The film is obtained by incorporating pullulan with a film coating base material such as methylcellulose.

JP-2000205-A2 discloses a perfume-containing coating for a soft capsule. The coating is obtained by adding a polyhydric alcohol to a pullulan solution containing an oily perfume and a surfactant such as a sugar ester having a high HLB.

U.S. Pat. No. 2,949,397 describes a method of making a mineral filled paper which comprises the step of coating finely divided mineral filler particles with an aqueous colloidal dispersion of plant mucilage in the form of substituted mannan selected from the group consisting of mannoglactans and gluco-glactans.

U.S. Pat. No. 3,871,892 describes the preparation of pullulan esters by the reaction of pullulan with aliphatic or aromatic fatty acids or their derivatives in the presence of suitable solvents and/or catalysers. The pullulan esters can be shaped by compression molding or extrusion at elevated temperatures or by evaporation of solvents from their solutions to form shaped bodies such as films or coatings.

U.S. Pat. No. 3,873,333 discloses adhesives or pastes prepared by dissolving or dispersing uniformly a pullulan ester and/or ether in water or in a mixture of water and acetone in an amount between 5 percent to 40 percent of the solvent.

U.S. Pat. No. 3,932,192 describes a paper coating material containing pullulan and a pigment.

U.S. Pat. No. 4,257,816 discloses a novel blend of algin, TKP, and guar gum which are useful in commercial gum applications, particularly for the paper-industry, where thickening, suspending, emulsifying, stabilizing, film-forming and gel-forming are needed.

U.S. Pat. No. 3,997,703 discloses a multilayered molded plastic having at least one layer comprising pullulan. and at least one layer selected from the group consisting of layers composed of homopolymers and copolymers of olefins and/or vinyl compounds, polyesters, polyamides, celluloses, polyvinylalcohol, rubber hydrochlorides, paper, and aluminum foil.

GB 1,533,301 describes a method of improving the water-resistance of pullulan by the addition of a water-soluble dialdehyde polysaccharides to pullulan.

GB 1559 644 also describes a method of improving the water-resistance of pullulan articles. The improved articles are manufactured by means of a process comprising bringing a mixture or shaped composition of a (a) pullulan or a water soluble derivative thereof and (b) polyuronide or a water-soluble salt thereof in contact with an aqueous and/or alcoholic solution of a di- or polyvalent metallic ion.

Although capsules were mentioned or claimed in these patents, their compositions do not have sufficient setting ability or none at all. Consequently, these compositions do not allow an industrial scale hard capsule production, and no attempt has been described to produce pullulan hard capsules by means of conventional dipping moulding processes.

Another problem with conventional pullulan hard capsules is their poor surface gliding performance, which leads to a high opening force of the pre-joint capsules and a high closing force. Indeed, these are two key parameters for a good filling performance on automatic high speed capsule filling equipment. During the filling process, the filling equipment opens, fills and recloses the capsules in an extremely high cadence. High opening or closing force can lead to defects such as non open, punched capsule ends and etc, and consequently to frequent machine stops.

The object of the present invention is therefore the provision of improved pullulan compositions which overcome the drawbacks of the prior art compositions. This object is solved according to the film forming composition, the container for unit dosage, the caplets, the capsules, the aqueous solutions, the use of the aqueous solutions for the manufacturing of hard capsules in a dip molding process, and the manufacturing of hard capsules from aqueous pullulan solutions according to the independent claims.

Further advantageous features, aspects and details of the invention are evident from the dependent claims, the description and the drawings. The claims are to be understood as a first non-limiting approach to define the invention in general terms.

The invention provides a film-forming composition comprising pullulan and a setting system. For example, a composition of this invention can contain from 85% to 95% by weight of pullulan and from 5% to 15% by weight of the setting system.

Surprisingly, we found that the addition of a very small amount of a setting system, preferably comprising hydrocolloids acting as a gelling agent, most preferably polysaccharides, confers an appropriate setting ability with cooling to pullulan solution so that the production of hard pullulan capsules can be produced with a conventional dip moulding process.

In a preferred embodiment, the film forming composition may preferably further contain a cation containing salt, comprising at least one cation. Optionally, the film forming composition may further comprise at least one sequestering agent.

In an aspect of the present invention the film compositions are used for the manufacturing of hard capsules by conventional dip moulding process as normally used in the production of conventional hard gelatine capsules.

In an additional aspect of the present invention there are provided aqueous solutions comprising the film forming compositions of the present invention for the manufacture of capsules. The setting system gets the solution to set on the dipped pins, thus assuring a uniform capsule shell thickness. The setting system is preferably composed of a gelling agent, such as said hydrocolloids or polysaccharides, and optionally salt and sequestering agent.

The cation containing salt in the composition serves to enhance the setting ability of the gelling agents. Preferably, the salt comprises cations such as $K^+$, $Li^+$, $Na^+$, $NH_4^+$, $Ca^{2+}$, or $Mg^{2+}$, etc. The amount of cations is less than 5% by weight, preferably less than 3%, more preferably 0.01% to 3% by weight, even more Preferably 0.5% to 2% by weight. especially 0.01 to 1% by weight in the aqueous pullulan solution. The preferred salt concentration in the solution is less than 2%.

In a further aspect of the present invention there are provided compositions for the use in pharmaceutical, veterinary, food, cosmetic or other products like films for wrapping food, aspics or jellies, preferably for predosed formulations like soft or hard capsules and wherein the pullulan compositions has in aqueous solution a sufficient setting ability.

In a particular aspect of the present invention there are provided containers for unit dosage forms for agrochemicals, seeds, herbs, foodstuffs, dyestuffs, pharmaceuticals, or flavoring agents produced from the film forming compositions of the present invention. Preferably, such containers are capsules, especially pharmaceutical capsules. The capsule halves of the capsules are preferably sealed with one or more layers of the film forming compositions of the present invention. The capsule halves are preferably sealed by means of a liquid fusion process. The capsules of the present invention may preferably release the product they are filled with at low temperatures, preferably at room temperature.

In a further aspect of the present invention there are provided caplets encapsulated in a film forming composition of the present invention.

Compared to gelatine or HPMC, the advantages of pullulan can be mentioned as follows:

Non-animal origin

No chemical modification, totally natural.

Higher product quality consistency by the fermentation process control.

High homogeneity and transparency of films

Very low oxygen permeability. Its capsules are particularly useful for the filling of oxygen sensitive products such as fish and vegetable oils.

Relatively low water content, lower than gelatine.

High stability of various properties over storage such as mechanical and dissolution properties.

The addition of a setting system, preferably based on polysaccharides, to pullulan solutions enables the adaptation of specific and desired gelling properties for the production of hard pullulan capsules by a conventional dipping process. For the production of such capsules it is extremely important that the film forming pullulan solution remaining on the mould pins after dipping is prohibited from flowing down the pins. Otherwise the obtained film will not have the desired uniform thickness.

Consequently the present invention enables that the hard pullulan capsules can be produced with the same equipment used for the production of conventional hard gelatine capsules in the same range of process conditions. Furthermore capsules produced from compositions of the present invention have the same dimensional specifications and allow the use of the existing filling machinery and do not require specific and new equipment for the filling process.

In an preferred embodiment of the present invention, the concentration of pullulan in the dipping aqueous solution is in a range of 10 to 60%, preferably 10 to 50%, more preferably 15 to 40%, and most preferably 10 to 40% by weight.

Although pullulan of various molecular weight is usable, pullulan has a viscosity from 100 cps to 2000 cps at above mentioned concentration and at dipping temperature (40–70° C.) is preferred.

The pullulan without desalting (Japanese food grade) is usable, however the desalted pullulan (Japanese pharmaceutical excipients grade) is preferable for its improved mechanical properties.

In preferred embodiments of the present invention the setting system comprises a hydrocolloid or mixtures of hydrocolloids.

Suitable hydrocolloids or mixtures thereof for the present invention, producing synergistic properties, may be selected from the group comprising natural seaweeds, natural seed gums, natural plant exudates, natural fruit extracts, biosynthetic gums, gelatines, biosynthetic processed starch or cellulosic materials, preferred are the polysaccharides.

In a preferred embodiment of the present invention, the polysaccharides are selected from the group comprising alginates, agar gum, guar gum, locust bean gum (carob), carrageenan, tara gum, gum arabic, ghatti gum, Khaya grandifolia gum, tragacanth gum, karaya gum, pectin, arabian (araban), xanthan, gellan, starch, Konjac mannan, galactomannan, funoran, and other exocellular polysaccharides. Preferred are exocellular polysaccharides.

Preferred exocellular polysaccharides for use in the present invention are selected from the group comprising xanthan, acetan, gellan, welan, rhamsan, furcelleran, succinoglycan, scleroglycan, schizophyllan, tamarind gum, curdlan, and dextran.

In a further preferred embodiment of the present invention the hydrocolloids of the setting system are kappa-carrageenan or gellan gum or combinations like xanthan with locust bean gum or xanthan with konjac mannan.

Among the setting systems mentioned above, the systems of kappa-carrageenan with cations and gellan gum with cations are specifically preferred. They produce high gel strength at low concentrations and have good compatibility with pullulan.

The amount of the setting agent is preferably in the range of 0.01 to 5% by weight and especially preferred 0.03 to 1.0% in the aqueous pullulan solution of the present invention.

In a further preferred embodiment of the present invention the sequestering agents are selected from the group comprising ethylenediaminetetraacetic acid, acetic acid, boric acid, citric acid, edetic acid, gluconic acid, lactic acid, phosphoric acid, tartaric acid, or salts thereof, methaphosphates, dihydroxyethylglycine, lecithin or beta cyclodextrin and combinations thereof. Especially preferred is ethylenediaminetetraacetic acid or salts thereof or citric acid or salts thereof.

In another preferred embodiment of the present invention, the amount of the sequestering agent is less than 5% by weight, preferably less than 3%, more preferably 0.01% to 3% by weight, even more preferably 0.5% to 2% by weight especially 0.01 to 1% by weight of the aqueous dipping solution.

In the case that gellan is used as gelling agent, the compositions preferably contain a sequestering agent to improve the capsule solubility. The preferred sequestering agents are ethylenediaminetetraacetic acid or salts thereof and citric acid and salts thereof. The amount is preferably less than 1% in the solution compositions.

The pullulan compositions of the present invention may in a further preferred embodiment additionally comprise pharmaceutically or food acceptable colouring agents in the range of from OX to 10% based upon the weight of the film. The colouring agents may be selected from the group comprising azo-, guinophthalone-, triphenylmethane-, xanthene- or indigoid dyes, iron oxides or hydroxides, titanium dioxide or natural dyes or mixtures thereof. Examples are patent blue V, acid brilliant green BS, red 2G, azorubine, ponceau 4R, amaranth, D+C red 33, D+C red 22, D+C red 26, D+C red 28, D+C yellow 10, yellow 2 G. FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, clorophyllin, canthaxanthin, caramel, or betanin.

The inventive pullulan compositions may in a further preferred embodiment additionally contain at least one pharmaceutically or food acceptable plasticiser or flavoring agent.

In yet another preferred embodiment of the present invention the pullulan containers, such as capsules may be coated with a suitable coating agent like cellulose acetate phthalate, polyvinyl acetate phthalate, methacrylic acid gelatines, hypromellose phthalate, hydroxypropylmethyl cellulose phthalate, hydroxyalkyl methyl cellulose phthalates, hydroxypropyl methylcellulose acetate succinate or mixtures thereof to provide e.g. enteric properties.

In a preferred embodiment of the present invention, the film-forming compositions further comprise one or more surfactants.

The surfactant in the compositions improves the capsule surface properties in such a way that the capsule works well on the conventional automatic high speed capsule filling equipment.

We have surprisingly found that the addition of a small quantity of selected surfactants of pharmaceutical or food quality, we can improve dramatically the pullulan film surface gliding performance, consequently to get the capsule opening and closing forces to the range required by filling equipment.

Therefore, the present invention provides compositions for hard pullulan capsules with improved surface properties containing pullulan, setting system and surfactant and the aqueous solutions of said film forming compositions for the manufacturing of the capsules.

With these preferably aqueous solutions, we can produce hard pullulan capsules with good filling performance by conventional dip mould process just like hard gelatine capsules.

A further percieved disadavantage of unmodified pullulan capsule film is its adhesive nature or tackiness when touched by hand. The rapid remoisturing properties of pullulan results in a percieved tackiness when holding the capsule film in the hand for 30 seconds or more.

An additional disadvantage is evident on swallowing the capsule film as the film may adhere to the tongue, palet (upper mouth), throat or oesophagus and compare unfavorably with traditional gelatin film capsules.

Patient compliance is a major advantage of the traditional hard gelatin capsule and supported by several market studies whcih cite "ease of swallow" as an important factor in patient preference for the capsule oral dosage form.

In order to solve this percieved disadvantage of pullulan capsule film, surprisingly it has been found that a surfactant content in the pullulan capsule film provides an acceptable temporary water-repellant surface for handling or swallowing the capsule. Additionally, the selected surfactant may be applied externally as a transparent coating in the range 0.5 to 100 microns. The selected surfactants are water soluble at 37 C.

The pullulan in the compositions is the base material for hard capsule making. Its preferred concentration in the aqueous solutions comprising the surfactant is from 10 to 40%.

The preferred gelling agents for the use with the surfactant are kappa-carrageenan and gellan with a concentration in the solutions 0.05–3%.

The surfactant in the compositions is aimed to improve th. capsule surface gliding performance, and 60 the capsule filling performance on filling equipment. The surfactant can be cationic, anionic, non-ionic or amphoteric, and preferably selected from pharmaceutical and food quality such as sodium lauryl sulphate (SLS), dioctyl sodium sulfosuccinate (DSS), benzalkonium chloride, benzethonium chloride, cetrimide (trimethyltetradecylammonium bromide), fatty acid sugar esters, glyceryl monooleate, polyoxyethylene sorbitan fatty acid esters, polyvinyl alcohol, dimethylpolysiloxan, sorbitan esters or lecithin. Its amount based on pullulan is preferably 0.01% to 3%.

The above mentioned and other features of the present invention will be better understood by reference to the following examples and the accompanying figure, in which:

FIG. 1 shows a graph listing dissolution test results of capsules according to the present invention filled with acetaminophen in deionized water at 37° C. (USP XXIII dissolution).

The following examples and tests, not limitative, demonstrate the pullulan capsule production and properties. Furthermore, the examples demonstrate the hard capsule making, the surface gliding improvement, and the capsule filling improvement.

EXAMPLE 1

1.0 kg of pullulan (PI-20, Japanese Pharmaceutical Excipients grade) powder is mixed with 10 g of kappa-carrageenan. To 4.0 kg of deionised water under stirring at room temperature is added 20 g of potassium acetate (0.2% by weight in the solution), followed by addition of the above mixture (20% of pullulan and 0.2% of carrageenan in the solution). The powder addition and stirring speeds should be very high in order to avoid the forming of lumps, which take a long time to be dissolved. The solution is heated up to 70° C. under stirring to totally dissolve the carrageenan and pullulan. It is possible to dissolve the components directly at 70° C., but the tendency of pullulan to lump is much higher.

The pullulan solution thus prepared is defoamed under slow stirring and then poured into a dipping dish of a pilot machine of conventional hard gelatine capsule production equipment. While keeping the dipping pullulan solution at 60° C., natural transparent hard pullulan capsules of size 0 were produced according to the conventional process with the same dimensional specifications to the conventional hard gelatine capsules.

EXAMPLE 2

1.0 kg of pullulan (PI-20) powder is mixed with 6 g of gellan. To 4.0 kg of deionised water under stirring at room temperature is added 20 g of potassium acetate (0.4% by weight in the solution) and 2 g of ethylenediaminetetraacetic acid disodium salt (0.04% in the solution), followed by addition of, the. above, mixture (20% of pullulan and 0.12% of gellan in the solution). Heat the solution up to 75° C. under stirring to dissolve totally the gellan and pullulan.

The pullulan solution thus prepared is defoamed under slow stirring and then poured into a dipping. dish of a pilot machine of conventional hard gelatine capsule production equipment. While keeping the dipping pullulan solution at 60° C., natural transparent hard capsules of size 0 were produced according to the conventional process with the same dimensional specifications to the conventional hard gelatine capsules.

Disintegration test results:

TABLE 1

Disintegration test results (according to USP XXIII 1995-<701> Disintegration):

| Capsule | Example 1 | Example 2 |
|---|---|---|
| Capsule emptied time | 3.0 min | 2.0 min |
| Total disintegration time | 10.0 min | 11.8 min |

Dissolution test results of capsules filled with acetaminophen in deionised water at 37° C. (USP XXIII dissolution) are represented in FIG. 1.

EXAMPLE 3

Pullulan film gliding improvement

In 400 g of demineralised water at room temperature were dispersed under stirring 0.05 g SLS (500 ppm/pullulan), 1 g of kappa-carrageenan (0.2%), 1.25 g of potassium acetate (0.25%) and 100 g of pullulan (20%). The mixture is heated is to 70° C. under stirring for complete solubilisation and then the stirring is reduced for defoaming. The solution then is used to cast on glass plates of 4 mm thickness to form pullulan films of about 100 µm thickness after drying at room conditions.

The pullulan film gliding performance is evaluated by a test on a slant d plan, a method commonly used by gelatine producers. The method determines the smallest angle of inclination of glass plate to provoke the gliding of a film coated glass plate over another one with films face to face. Consequently, the smaller the gliding angle, the better the film gliding performance.

Repeat the above example with surfactant contents listed in Table 2.

In Table 2, we gathered the gliding performance for different surfactants and quantity.

TABLE 2

| Surfactant | Pullulan gliding performance (*) | | | |
|---|---|---|---|---|
| | No | 500 ppm | 1000 ppm | 5000 ppm |
| SLS | 29 | 9 | 5 | 6 |
| Hydrolysed deoil lecithin | | 9 | 9 | 7 |
| Polysorbate 20 | | 12 | 12 | |
| Polysorbate 80 | | 10 | 9 | |
| Sorbitan laurate | | 10 | 8 | |
| Sorbitan oleate | | 9 | 7 | |

EXAMPLE 4

Pullulan capsule production and performance

In 142 liters of demineralised water at room temperature were dispersed under stirring 20 g hydrolysed deoil lecithin (500 ppm/pullulan), 363 g kappa-carrageenan (0.2%) and 40 kg pullulan (22%). The mixture is heated up to 70° C. under stirring for total solubilisation. 455 g potassium acetate previously dissolved in some water was then added into the solution. A slurry made with 800 g $TiO_2$, 3 liters hot water and 3 liters so prepared pullulan solution by high shearing was added into the solution in order to produce white opaque capsules. After defoaming, the solution is finally stabled at 60° C.

A second identical preparation was made. The two preparations were used to feed a conventional hard gelatine capsule production machine, white opaque hard pullulan capsules were then produced in the similar way to hard gelatine capsules.

As reference, transparent pullulan hard capsules without surfactant in the formulation were produced in the same way as above.

The improvement of hard pullulan capsules by the addition of surfactant is illustrated by the data gathered in Table 3, and was confirmed by a filling trial on a filling equipment KGF400.

TABLE 3

| Capsule | Opening force of pre-lock capsule | Closing force |
|---|---|---|
| Capsule of example 2 | 12 g | 6.0 N |
| Reference capsule | 36 g | 7.6 N |

What is claimed is:

1. A film forming composition comprising pullulan and a setting system wherein the setting system further comprises cations.

2. The film forming composition according to claim 1, wherein the cations are preferably selected from the group consisting of K+, Na+, Li+, $NH_4$+, Ca++ and Mg++.

3. The film forming compositions according to claim 1, wherein the setting system further comprises at least one sequestering agent.

4. The film forming composition according to claim 3, wherein the at least one sequestering agent is selected from the group consisting of ethylenediaminetetraacetic acid, acetic acid, boric acid, citric acid, edetic acid, gluconic acid, lactic acid, phosphoric acid, tartaric acid, or salts thereof, methaphosphates, dihydroxyethylglycine, lecithin or beta cyclodextrin.

5. The film forming composition according to claim 1, wherein the setting system comprises hydrocolloids.

6. The film forming composition according to claim 5, wherein the hydrocolloids of the setting system are polysaccharides.

7. The film forming composition according to claim 5, wherein the hydrocolloids of the setting system are exocellular polysaccharides.

8. The film forming composition according to claim 1, wherein the pullulan is 85% to 95% by weight, and the setting system is 0.01% to 5% by weight.

9. The film forming composition according to claim 1, wherein the amount of cations are less than 5% by weight.

10. The film forming composition according to claim 3, wherein the sequestering agent is less than 5% by weight.

11. The film forming composition according to claim 5, wherein the hydrocolloids of the setting system are selected from the group consisting of alginates, agar gum, guar gum, locust bean gum (carob), carrageenan, tara gum, gum arabic, ghatti gum, Khaya grandifolia gum, tragacanth gum, karaya gum, pectin, arabian (araban), xanthan, gellan, starch, Konjac mannan, galactomannan, or funoran.

12. The film forming composition according to claim 5, wherein the hydrocolloids of the setting system are selected from the group consisting of xanthan, acetan, gellan, welan, rhamsan, furcelleran, succinoglycan, scleroglycan, schizophyllan, tamarind gum, curdlan, or dextran.

13. The film forming composition according to claim 5, wherein the hydrocolloids of the setting system are selected from the group consisting of gellan gum or kappa-carrageenan.

14. The film forming composition according to claim 1, further comprising plasticizers or/and flavoring agents.

15. The film forming composition according to claim 1, further comprising colouring agents in a range from about 0% to 10% based upon the weight of the composition.

16. The film forming composition according to claim 15 wherein the colouring agent or mixture of colouring agents is selected from the group comprising consisting of azo-, quinophthalone-, triphenylmethane-, xanthene- or indigoid dyes, iron oxides or hydroxides, titanium dioxide or natural dyes.

17. The film composition according to claim 16 wherein the colouring agent or mixture of colouring agents is selected from the group consisting of patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3 or brilliant black BN.

18. The film forming composition according to claim 16 wherein the colouring agent or mixture of colouring agents is selected from the group consisting of carbon black, iron oxide black, iron oxide red, iron oxide yellow, titanium dioxide, riboflavin, carotenes, anthocyanines, turmeric, cochineal extract, clorophyllin, canthaxanthin, caramel, or betanin.

19. The film forming composition according to claim 1, wherein the composition comprises one or more surfactants.

20. The film forming composition according to claim 19, wherein the surfactant is selected from the group consisting of sodium lauryl sulphate (SLS), dioctyl sodium sulfosuccinate (DDS), benzalkonium chloride, benzethonium chloride, cetrimide (trimethyltetradecylammonium bromide), fatty acid sugar esters, glyceryl monooleate, polyoxyethylene sorbitan fatty acid esters, polyvinyl alcohol, dimethylpolysiloxan, sorbitan esters or lecithin.

21. The film forming composition according to claim 19, wherein the surfactant is 0.01 to 3% by weight relative to the amount of pullulan.

22. A container for unit dosage forms for agrochemicals, seeds, herbs, foodstuffs, dyestuffs, pharmaceuticals, or flavouring agents produced from the film forming composition according to claim 1.

23. The container according to claim 22 wherein said container is a capsule.

24. The container according to claim 22, wherein the container comprises a coating.

25. The container according to claim 24, wherein the coating is selected from the group consisting of cellulose acetate phthalate, polyvinyl acetate phthalate, methacrylic acid gelatines, hypromellose phthalate, hydroxypropylmethyl cellulose phthalate hydroxyalkyl methyl cellulose phthalates, hydroxypropyl methylcellulose acetate succinate and mixtures thereof.

26. The container according to claim 24, wherein the coating is a surfactant.

27. The container according to claim 26, wherein the coating is in the range of 0.5 to 100 microns.

28. The container according to claim 26, wherein the surfactant is selected from the group consisting of sodium lauryl sulphate (SLS), dioctyl sodium sulfosuccinate (DDS), benzalkonium chloride, benzethonium chloride, cetrimide (trimethyltetadecylammonium bromide), fatty acid sugar esters, glyceryl monooleate, polyethylene sorbitan fatty acid esters, polyvinyl alcohol, dimethylpolysiloxan, sorbitan esters or lecithin.

29. A caplet encapsulated in a film forming composition according to claim 1.

30. A container comprising two halves forming a capsule, wherein the container is sealed with one or more layers of the composition according to claim 1.

31. The container according to claim 30 wherein the capsule halves are sealed by a liquid fusion process.

32. The container according to claim 22, wherein a product filled in the container is releasable at a low temperature.

33. An aqueous solution for the manufacturing of capsules comprising the film forming composition according to claim 1.

34. The aqueous solution according to claim 33, further comprising pullulan in an amount of from 10 to 60%, by weight of the aqueous solution.

35. The aqueous solution according to claim 33 further comprising at least one setting agent in an amount of 0.01 to 5% by weight of the aqueous solution.

36. The aqueous solution according to claim 33, further comprising cations in an amount less than 3%, by weight of the aqueous solution.

37. The aqueous solution according to claim 33, further comprising at least one sequestering agents in an amount less than 3%, by weight of the aqueous solution.

38. The film forming composition according to claim 1 wherein the amount of cations are 0.01% to 3% by weight.

39. The film forming composition according to claim 1 wherein the amount of cations are 0.5% to 2% by weight.

40. The film forming composition according to claim 3 wherein the sequestering agent is from 0.01% to 3% by weight.

41. The film forming composition according to claim 3 wherein the sequestering agent is from 0.5% to 2% by weight.

42. The container according to claim 22 wherein said container is a pharmaceutical capsule.

43. The aqueous solution according to claim 33, further comprising pullulan in an amount of from 15 to 40% by weight of the aqueous solution.

44. The aqueous solution according to claim 33, further comprising cations in an amount from 0.01 to 1% by weight of the aqueous solution.

45. The aqueous solution according to claim 33, further comprising at least one sequestering agent in an amount from 0.01 to 1% by weight of the aqueous solution.

46. The aqueous solution according to claim 33, further comprising at least one setting agent in an amount of 0.03 to 1.0% by weight of the aqueous solution.

* * * * *